United States Patent [19]
Bleiweiss et al.

[11] Patent Number: 5,837,701
[45] Date of Patent: Nov. 17, 1998

[54] COMPOSITION AND METHOD FOR TREATING CONDITIONS ASSOCIATED WITH SYMPTOMS OF UNSPECIFIED RETARDED MATURATION

[76] Inventors: Eduardo Samuel Bleiweiss; Daniel Gustavo Bleiweiss; Herman Bleiweiss, all of AV. Santa Fe 931, Buenos Aires, Argentina, 1059

[21] Appl. No.: 599,294

[22] Filed: Feb. 9, 1996

[30] Foreign Application Priority Data

Oct. 2, 1995 [AR] Argentina ................... 330996

[51] Int. Cl.⁶ ............... A61K 31/55; A61K 31/495; A61K 31/44; A61K 31/135
[52] U.S. Cl. ............. 514/217; 514/253; 514/345; 514/649
[58] Field of Search .................. 514/217, 253, 514/345, 649

[56] References Cited

U.S. PATENT DOCUMENTS 5,607,967  3/1997  Friedman et al. ............. 514/461

*Primary Examiner*—Theodore J. Criares
*Attorney, Agent, or Firm*—Evelyn M. Sommer

[57] ABSTRACT

Compositions and method for treating conditions in humans associated with symptoms of unspecified retarded maturation due to chromosomal abnormalities cerebral atrophy, Huntington's Chorea, Alzheimer's disease and the like wherein the composition comprises a) at least one of haloperidol, imipramine and trifluoperazine, b) gamma butyric acid, c) phenylalamine, d) an antioxidant, e) folic acid, f) nicotinamide or its salt and g) a lithium salt. The composition can additionally contain a benzodiazepine and is administered orally.

7 Claims, 18 Drawing Sheets

NORADRENALINE IN FRAGILE X SYNDROME

COMPOSITION AND METHOD FOR TREATING CONDITIONS ASSOCIATED WITH SYMPTOMS OF UNSPECIFIED RETARDED MATURATION

BACKGROUND OF THE INVENTION

In general, the patients included in this study had received different types of medication, without any positive results. The medication they received most was anticonvulsives and neuroleptics.

Some comments about other treatments are the following: in young patients suffering from mental retardation with fragile X syndrome, treatment with folic acid was suggested by Lejeune in 1982. However, in control studies no improvement in mental coefficient was disclosed (Turner et al 1980, Hagerman et al 1986, Fisch et al 1988).

However it seemed that some patients improve from their hyperactivity. Also stimulating drugs were used with same results, but they can be considered on the basis of individual results (Gustavson et al 1985).

However the fact that some boys and especially girls are carriers of the fragile X chromosome, without any clinical expression, may suggest that this syndrome is susceptible to the effect of the environment or to pharmacological treatment (Genetics of Neuropsychiatric diseases, Ed. Lennart, Wetterburg, 1988, The Macmillian Press Ltd. p. 117).

These treatments are applied to patients with retarded maturity of different etiologies. In reference to patients with dementia illness, especially patients with Alzheimer's type disease, behavior is variable, and they could be showing disorientation from mild to severe. In patients with this type of illness, symptoms are generally nonspecific and the patient might be agitated and at the same time he may have trouble sleeping. In general psychotropics are used in low dosage. We have to keep in mind that most of the psychotropic drugs have action over the neurotransmitters, and also produce extrapyramidal side effects.

When a drug is used during a test and does not produce an improvement, then a different drug should be used. Unfortunately, results of specific drugs to treat different symptoms of dementia are difficult to prove (Handbook of dementing illnesses, Ed. John C. Morris, 1994, Marcel Dekker, page 591).

From the different tests it is find out the difficulties to board any therapeutic treatment. One difficulty and not the least is to do a good diagnosis, since patients with different etiologies are frequently confused. So our effort was in the direction of the diagnosis and then to the treatment.

SUMMARY OF THE INVENTION

One of the objectives of this invention is a pharmaceutical composition, useful for the treatment of patients who are suffering from deletions, fragility of the X chromosome, or other chromosomic anomalies, cerebral atrophy or of the cerebellum; patients with unspecified retarded maturities or affected by Alzeheimer's Disease or Huntington's Chorea, or those who show similar symptoms of muscular hypotonia and similar states.

This composition includes at least one of the following drugs:

a) Haloperidol(4-(4-(4-Chlorophenyl)-4-Hydroxypiperidinyl)-1-(4-Fluorophenyl)-1-Butanone;
b) Imipramine (10,11-Dihydro-N,N-Dimethyl-5H-Dibenz(b,f)-Flazepine-5-Propanamine;
c) Trifluoperazine (10-(3-(4-Methyl-Piperazinyl)-Propyl)-2-Trifluoromethyl)-10H-Phenothiazine; and also:
d) Gamma Amino Butyric Acid;
e) Phenylalanine;
f) Anti oxidizing agents selected from Ascorbic Acid, Vitamin E and mixtures of the same;
g) Folic Acid;
h) Nicotinamide or the acceptable pharmaceutical salts of the same, and
i) Lithium salts, in combination with an acceptable pharmaceutical vehicle.

Another purpose of this invention is a pharmaceutical composition useful for treating patients suffering from the aforementioned pathologies, in doses which include at least one of the following drugs:

a) 0.01 to 3 mg of Haloperidol;
b) 3 to 8 mg of Imipramine;
c) 0.1 to 0.5 mg of Trifluoperazine; and also
d) 0.05 to 200 mg of Gama Amino Butyric Acid;
e) 1 to 10 mg of Phenylalanine;
f) 50 to 300 mg of anti oxidizing agents, selected from Vitamin E, Ascorbic Acid and mixtures of the same;
g) 100 to 300 mg of Folic Acid;
h) 0.05 to 0.5 mg of Nicotinamide or acceptable pharmaceutical salts of the same;
i) 25 to 100 mg of Lithium salts, such as Lithium Carbonate, Lithium Chloride or Bromide, Lithium Acetate.

Yet another purpose of this invention is a composition formulated in doses, each one of which include at least one of the following:

a) 0.02 mg of Haloperidol;
b) 5 mg of Imipramine;
c) 0.2 mg of Trifluoperazine; and also
d) 0.100 mg of Gamma Amino Butyric Acid;
e) Phenylalanine;
f) Anti oxidizing agents selected between Ascorbic Acid, Vitamin E and mixtures of the same;
g) 200 mg of Folic Acid;
h) 0.100 mg of Nicotinamide;
i) 50 mg of Lithium Carbonate, in a pharmaceutically acceptable vehicle.

Another purpose of this invention is a method for treating patients suffering from chromosomic deletions, fragility or aberrations, cerebral or cerebellar atrophy, patients with unspecified retarded maturities or suffering from Alzheimer's Disease, Huntington's Chorea or who show similar symptoms to muscular hypotonia or conscious states similar to those shown by patients suffering from the aforementioned diseases which include administering effective non toxic quantities of at least one of the following:

a) Haloperidol (4-(4-(4-Chlorophenyl)-4-y Hydroxy Piperidine)-1-(4-Fluorophenyl)-1-Butanone
b) Imipramine (10,11-dihydro-N,N-Dimethyl-5H-Dibenz (b,f)-Flazepine-5-Propanamine;
c) Trifluoroperazine (10-(3-(4-methyl-1-Piperazine)-(Propyl)-2-Trifluoromethyl)-10 H-Phenothiazine; and also:
d) Gamma Amino Butyric Acid;
e) Phenylalanine;
f) Anti oxidizing agents selected between Ascorbic Acid, Vitamin E and mixtures of the same;
g) Folic Acid;

h) Nicotinamide or the acceptable pharmaceutical salts of the same, and i) Lithium salts, in combination with an acceptable pharmaceutical vehicle, which includes in the treatment the administration of benzodiazepines, e.g. Lorazepan 5 to 10 mg/daily, or Diazepam 1 to 3 mg/daily.

Yet another purpose of this invention is treating patients suffering from chromosomic aberrations, cerebral or cerebellar atrophy; or suffering from diseases or who show symptoms of the aforementioned muscular hypotonia, which includes administering to patients, doses of a therapeutical composition in an acceptable pharmaceutical vehicle, which includes at least one of the following drugs:

a) 0.01 to 3 mg of Haloperidol;
b) 3 to 8 mg of Imipramine;
c) 0.1 to 0.5 mg of Trifluoroperazine;
d) 0.05 to 200 mg of Gamma Amino Butyric Acid;
e) Phenylalanine;
f) 50 to 300 mg of anti oxidizing agents, selected from Vitamin E, Ascorbic Acid and mixtures of the same;
g) 100 to 300 mg of Folic Acid;
h) 0.05 to 0.5 mg of Nicotinamide or pharmaceutically acceptable salts of the same;
i) 25 to 100 mg of Lithium salts, such as Lithium Carbonate or Lithium Bromide, Lithium Acetate, and including the administration of benzodiazepines, e.g. Lorazepan 5 to 10 mg/daily, or Diazepam 1 to 3 mg/daily.

An ulterior purpose of this invention is a method for treating the aforementioned pathologies, administering to affected patients doses of a pharmaceutical composition, which includes, in a pharmaceutically acceptable vehicle:

a) 0.02 mg of Haloperidol;
b) 5 mg of Imipramine;
c) 0.2 mg of Trifluoroperazine;
d) 0.100 mg of Gamma Amino Butyric Acid;
e) Phenylalanine;
f) Anti oxidizing agents
g) 200 mg of Folic Acid;
h) 0.100 mg of Nicotinamide;
i) 50 mg of Lithium Carbonate in a pharmaceutically acceptable vehicle.

A BRIEF DESCRIPTION OF THE FIGURES

FIG. 1. Phenyethylamine in fragile X syndrome.

FIG. 2. Dopamine in fragile X syndrome.

FIG. 3. Phenylacetic acid in fragile X syndrome.

FIG. 4. Dimethyltriptamine in fragile X syndrome.

FIG. 5. Adrenaline in fragile X syndrome.

FIG. 6. Noradrenaline in fragile X syndrome.

FIG. 7. Adrenaline in mental retardation without fragile X syndrome.

FIG. 8. Noradrenaline in mental retardation without fragile X syndrome.

FIG. 9. Phenyethylamine in mental retardation without fragile X syndrome.

FIG. 10. Dopamine in mental retardation without fragile X syndrome.

FIG. 11. Dimethyltriptamine in mental retardation without fragile X syndrome.

FIG. 12. Phenylacetic acid in mental retardation without fragile X syndrome.

FIG. 13. Adrenaline in Alzheimer's Disease.

FIG. 14. Noradrenaline in Alzheimer's Disease.

FIG. 15. Dopamine in Alzheimer's Disease.

FIG. 16. Phenylethylamine in Alzheimer's Disease.

FIG. 17. Dimethyltriptamine in Alzheimer's Disease.

FIG. 18. Phenylacetic acid in Alzheimer's Disease.

DETAILED DESCRIPTION OF THE INVENTION

Figure 1:
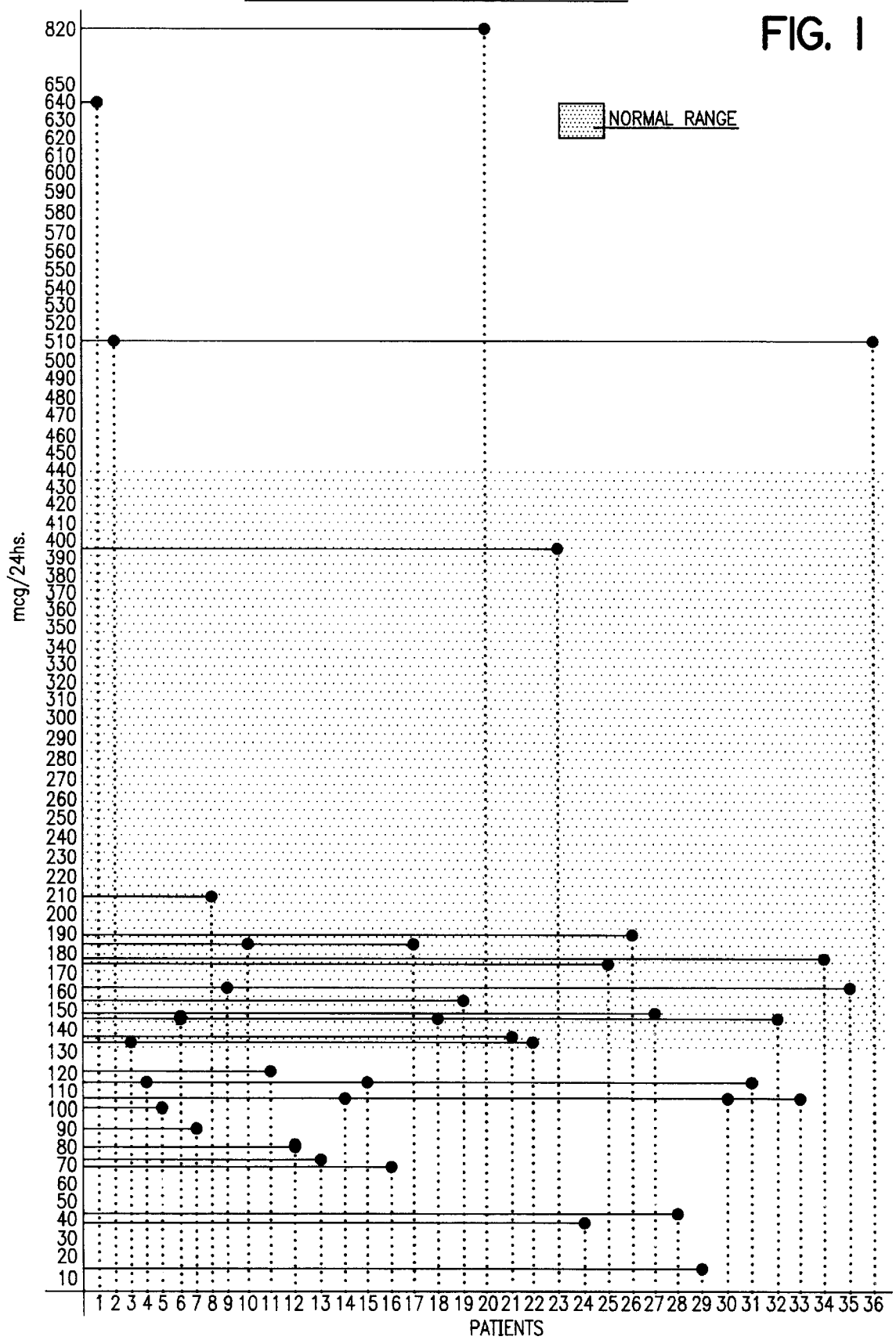
Figure 2:
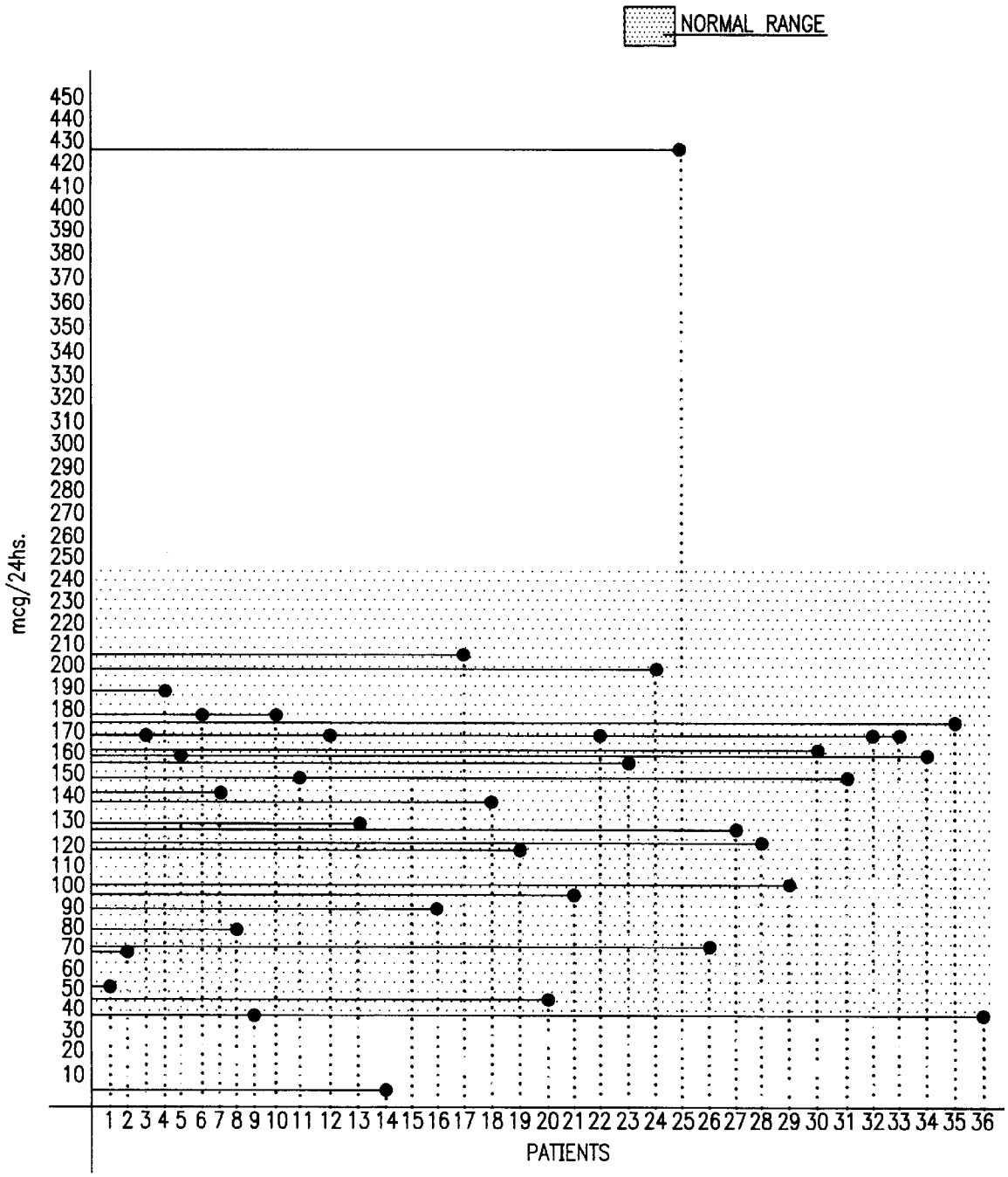
Figure 3:
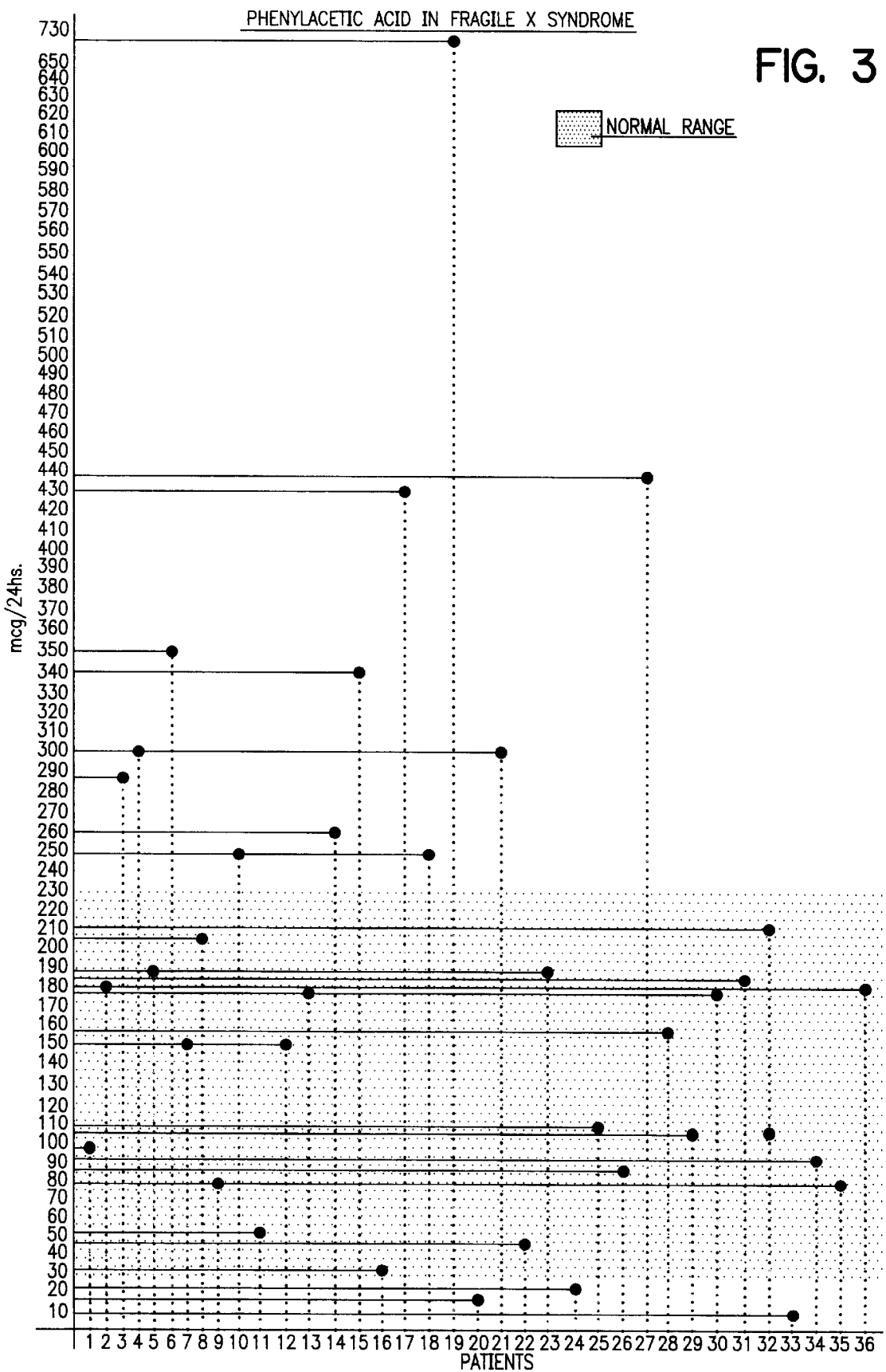
Figure 4:
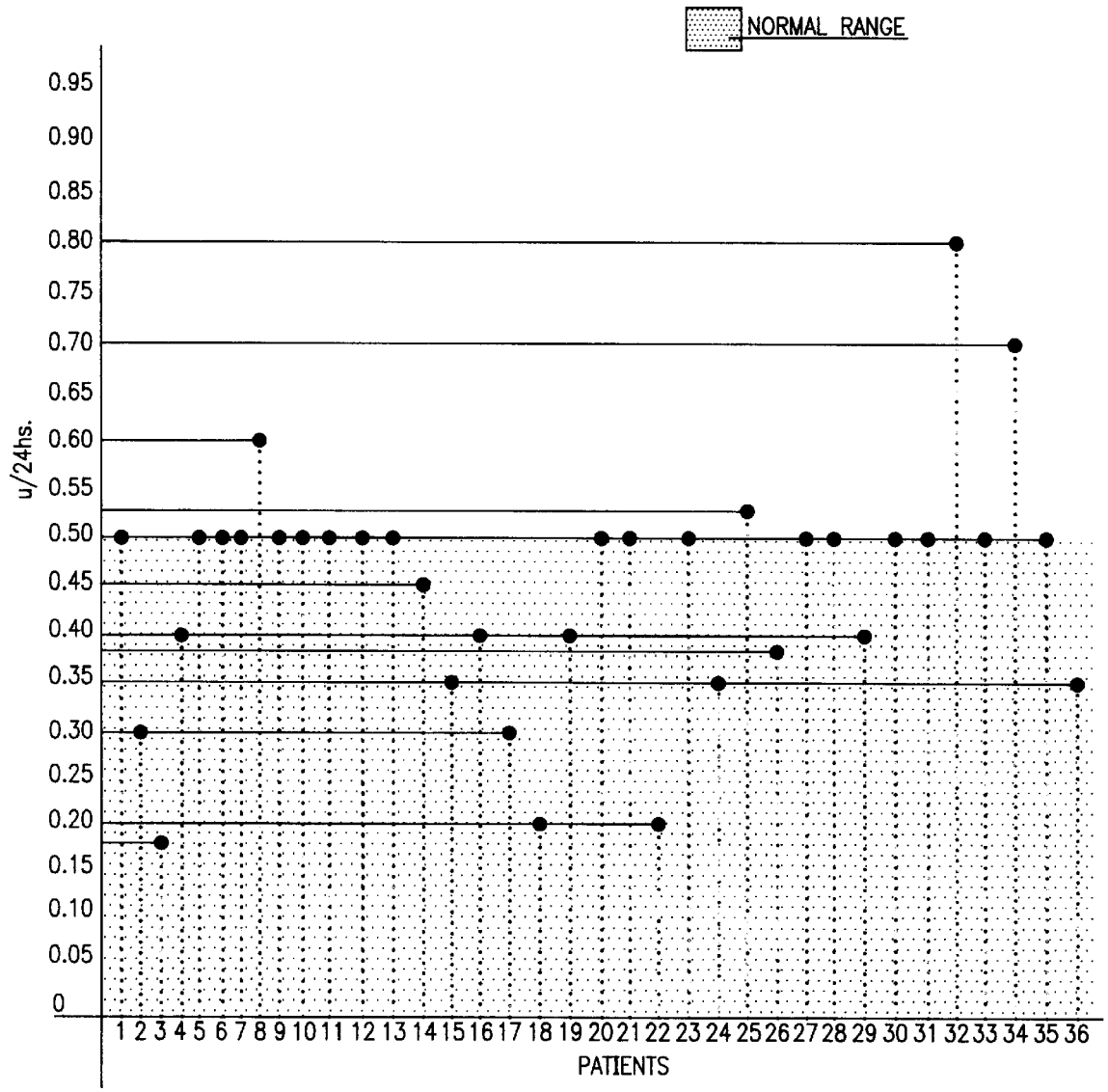
Figure 5:
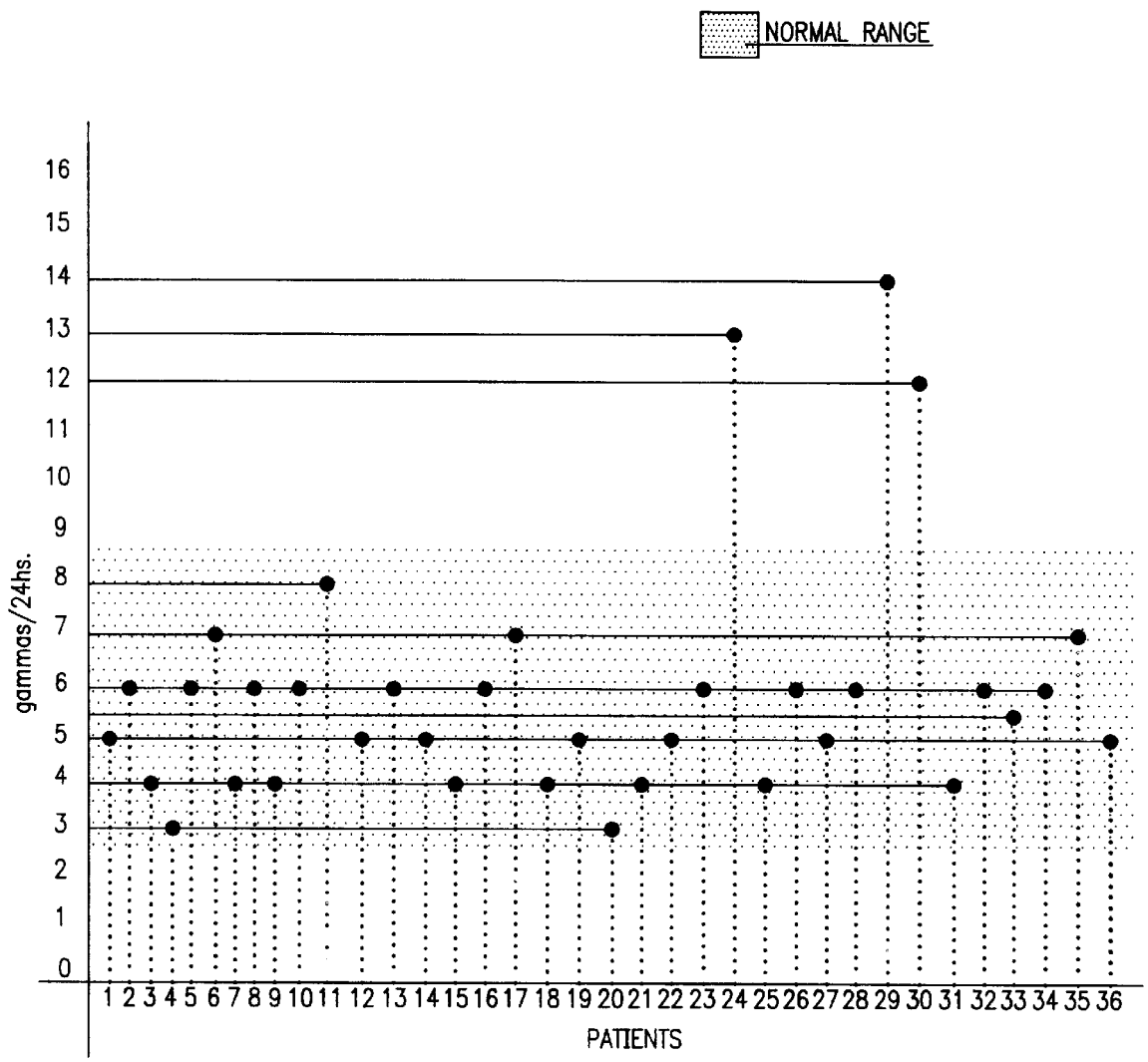
Figure 6:
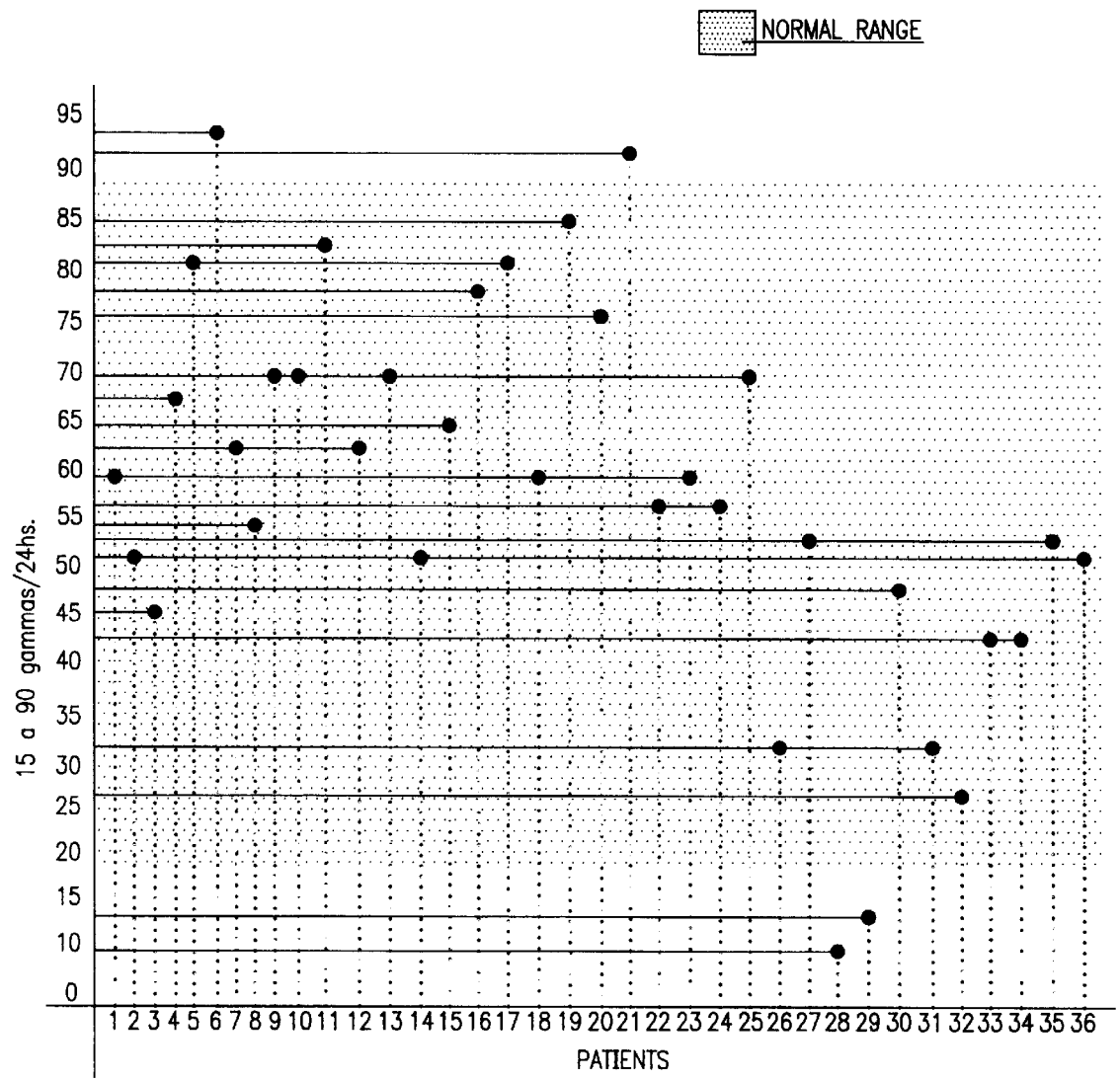
Figure 7:
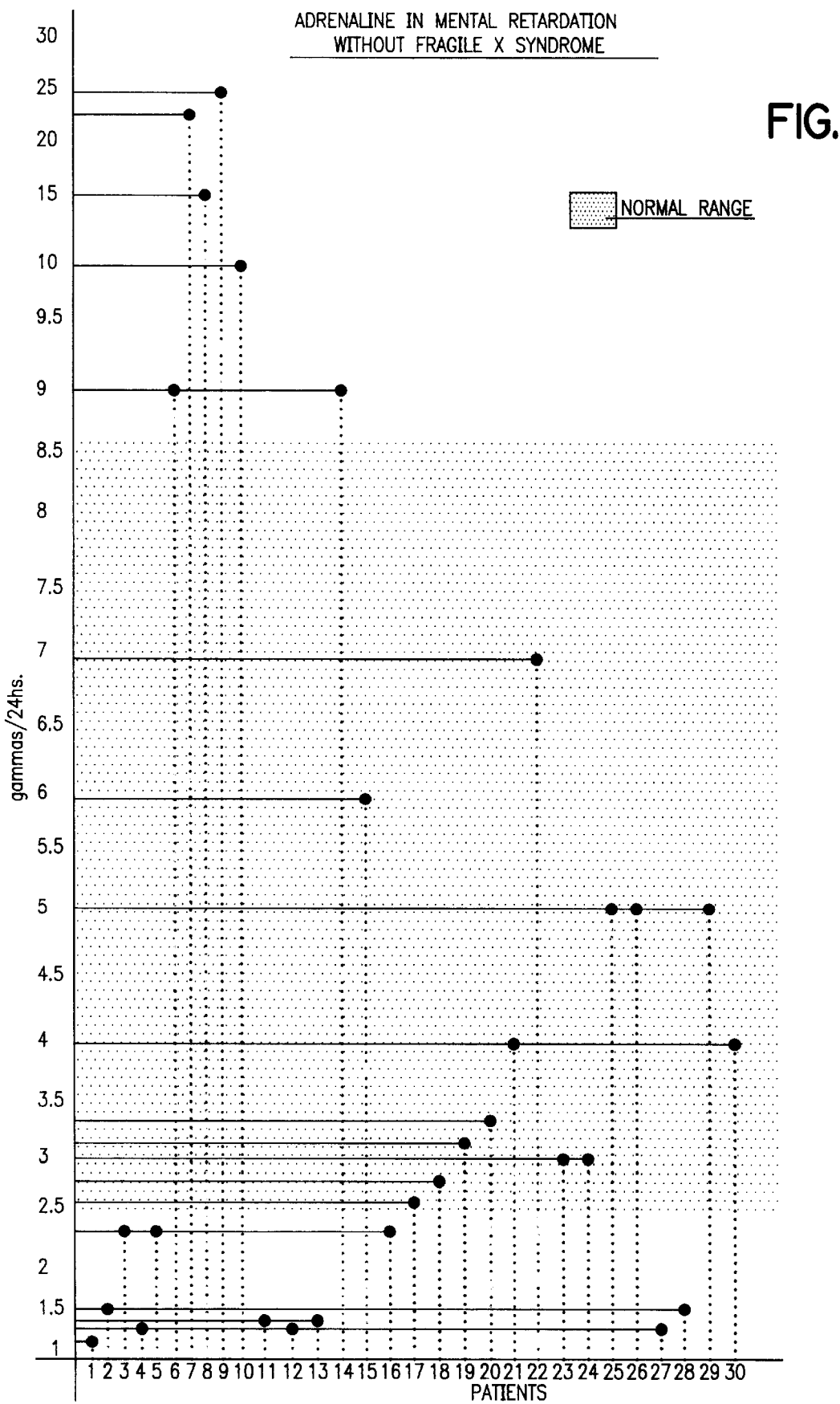
Figure 8:
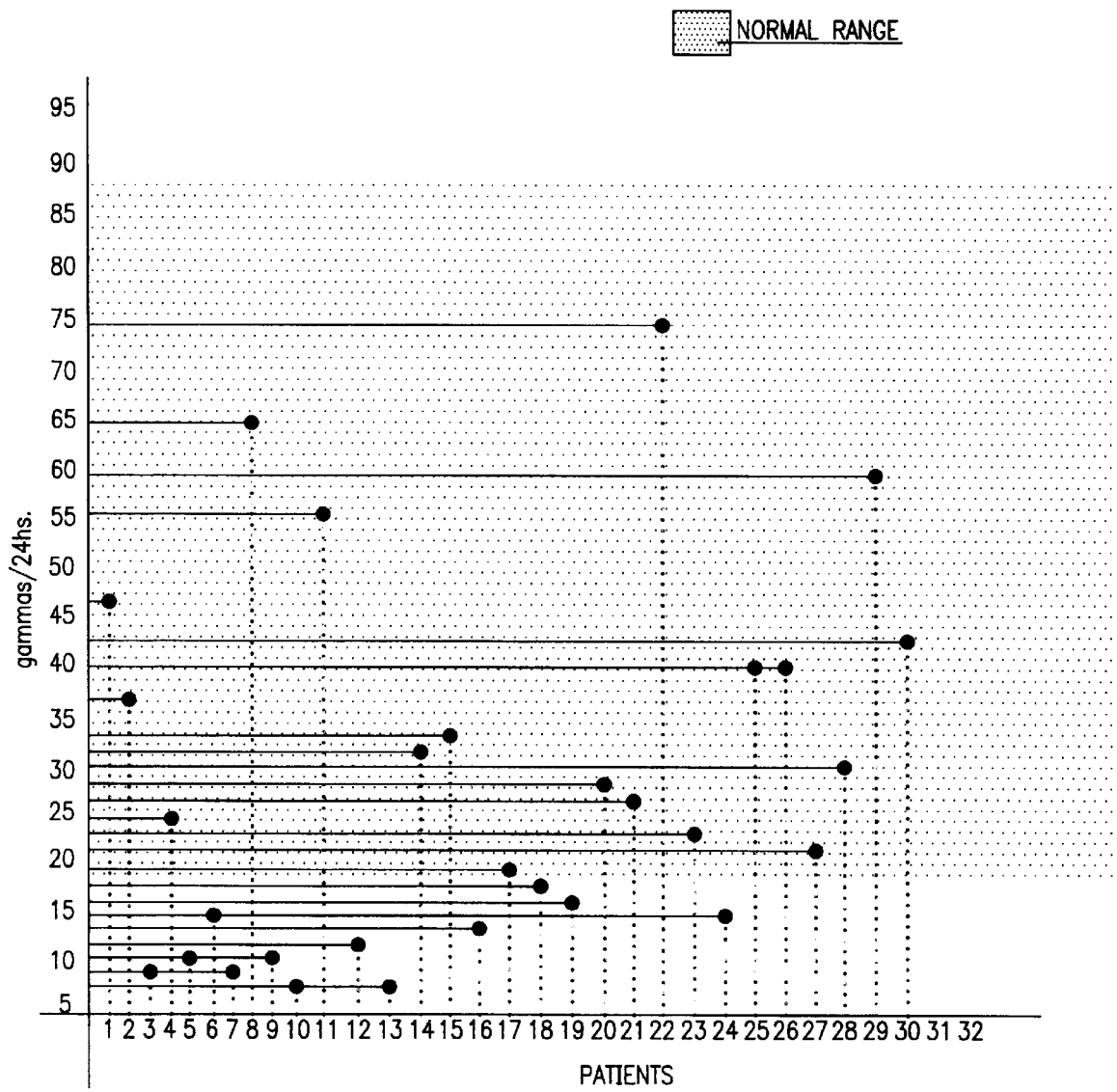
Figure 9:
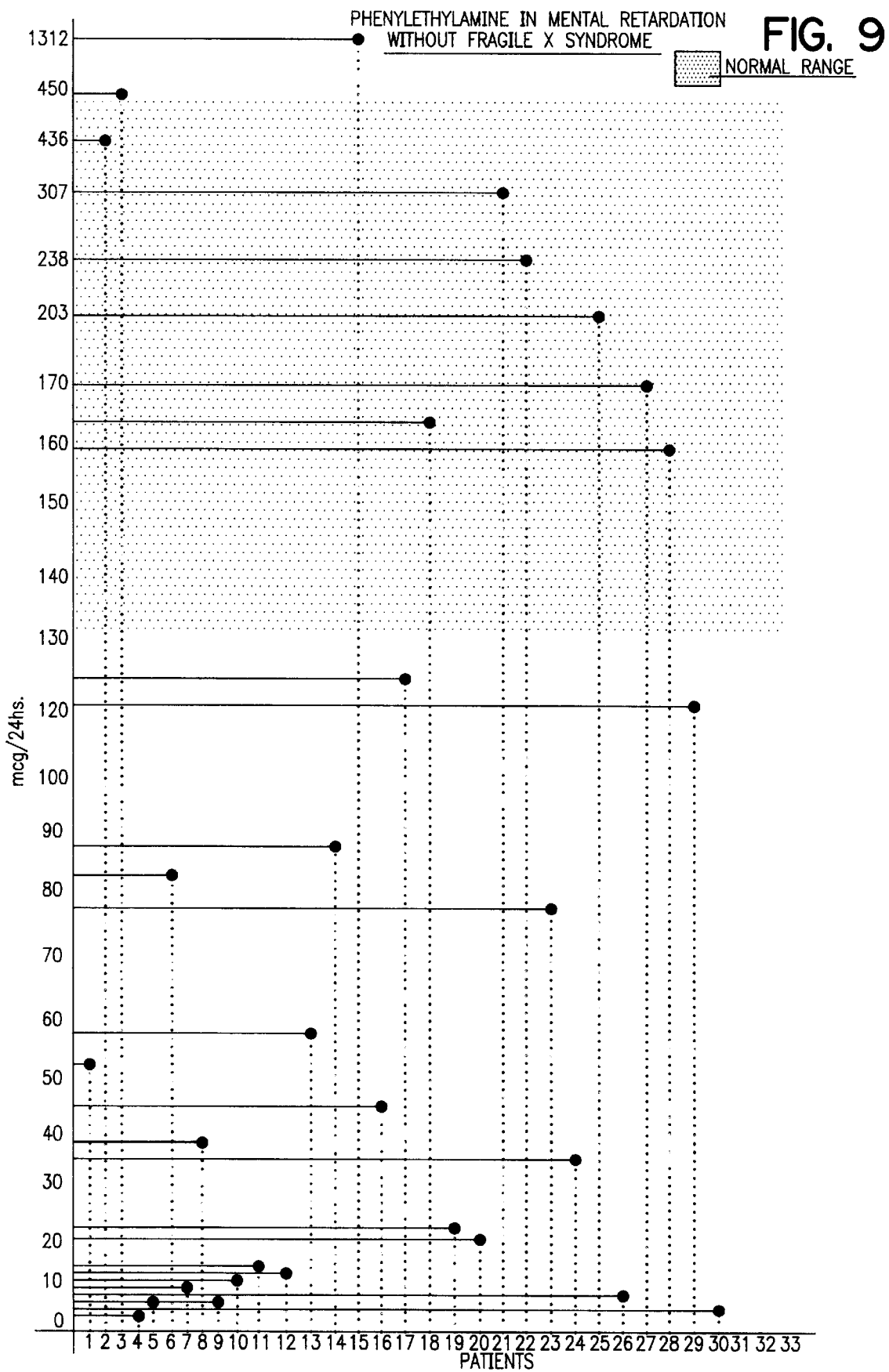
Figure 10:
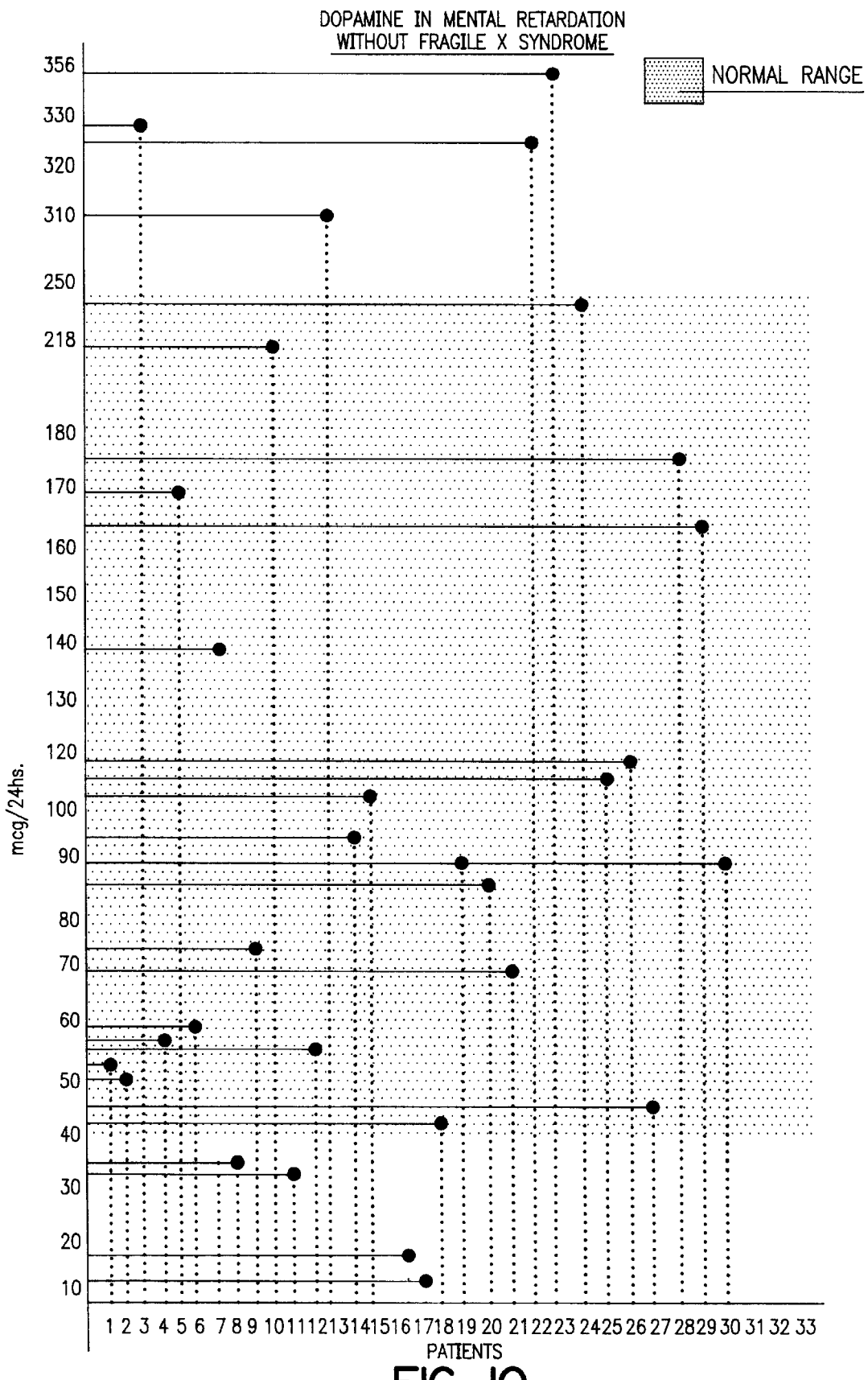
Figure 11:
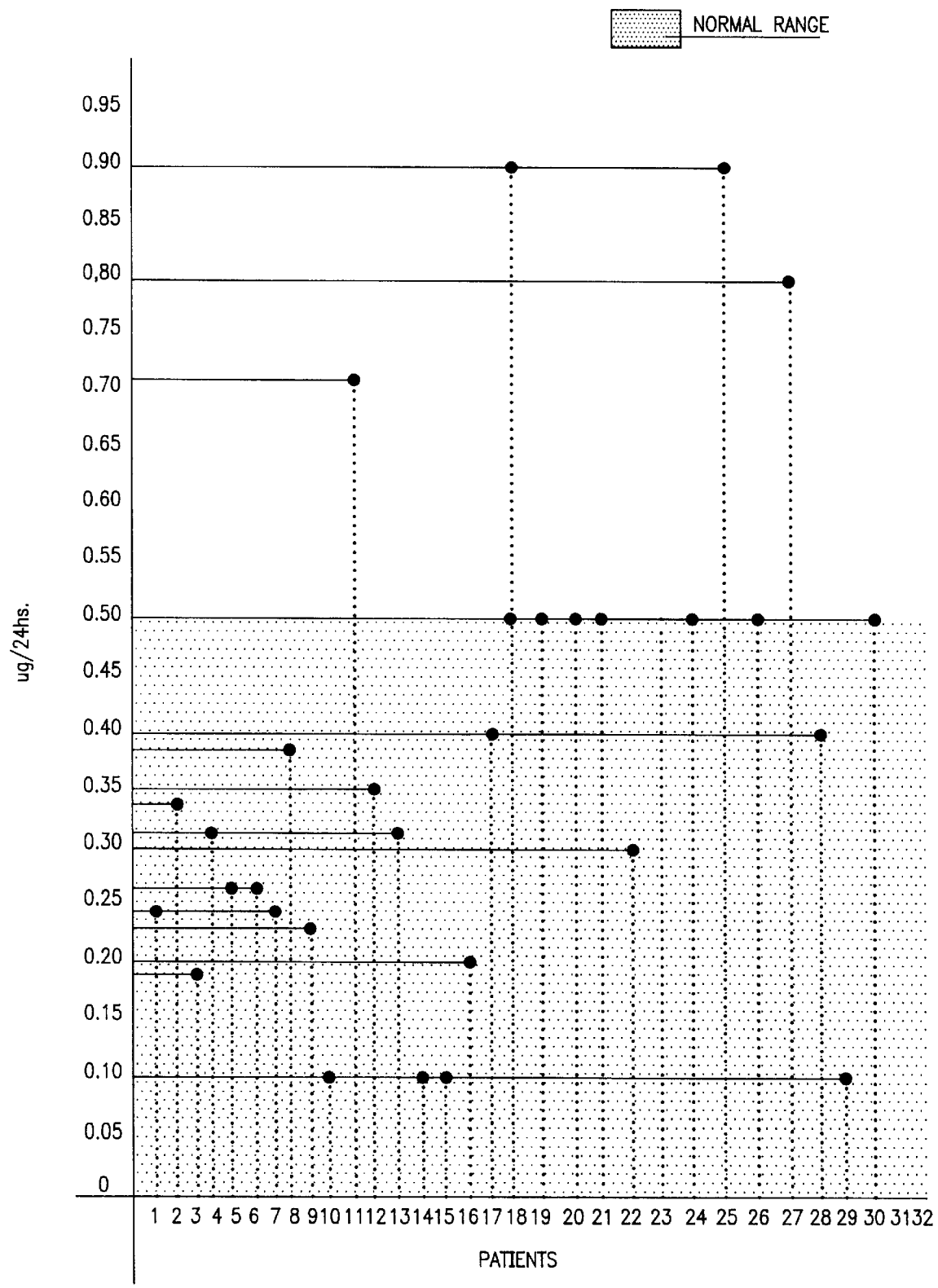
Figure 12:
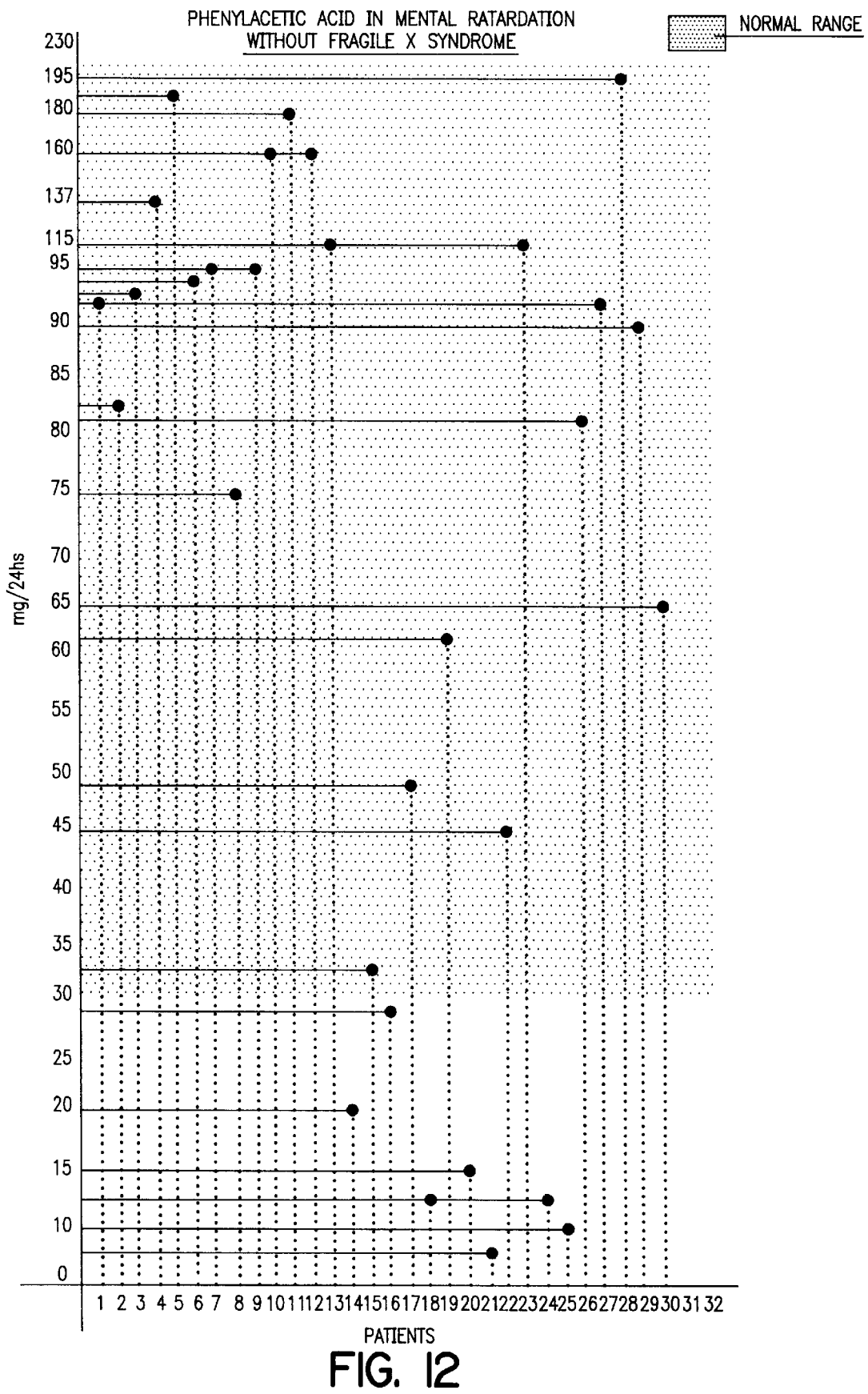
Figure 13:
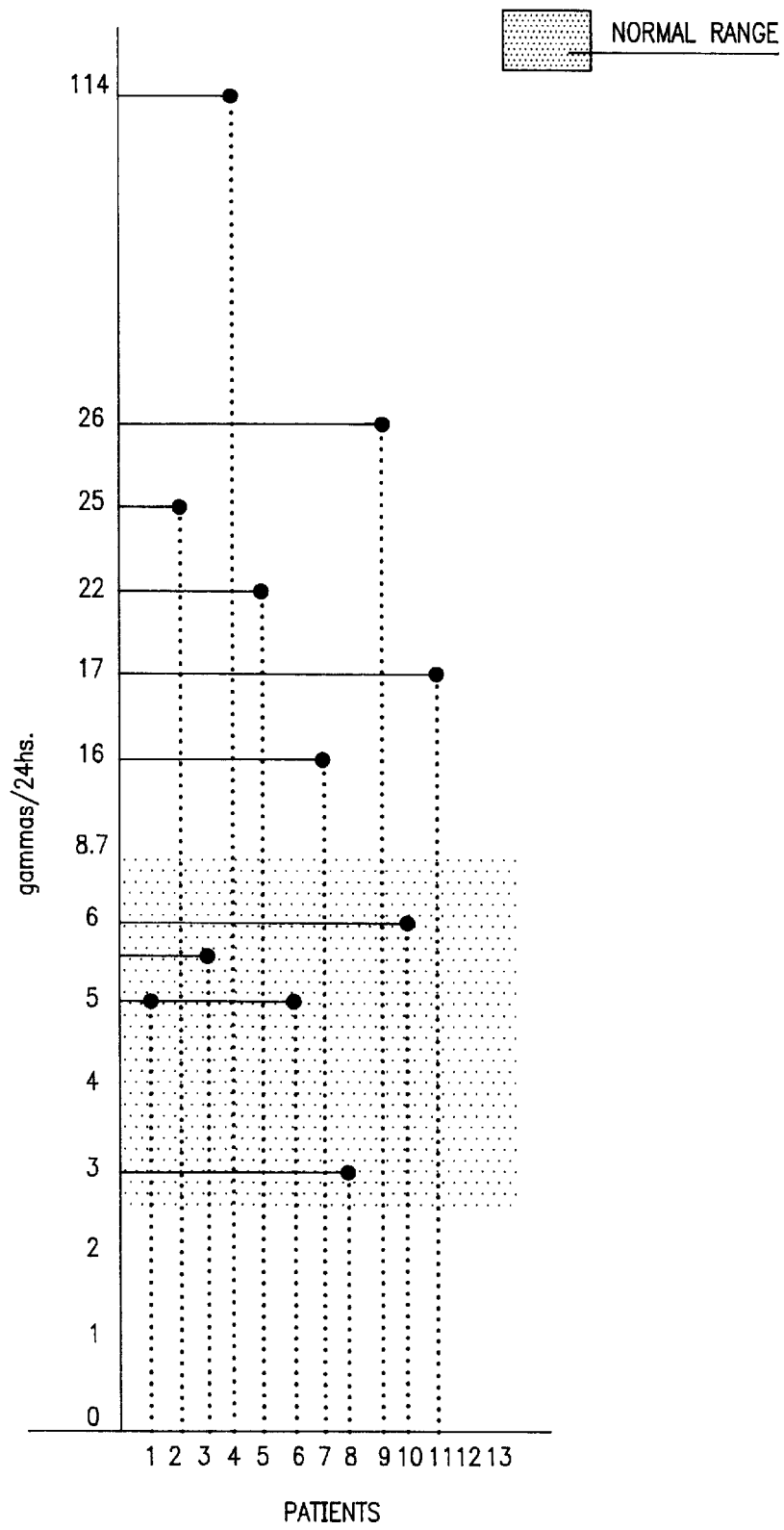
Figure 14:
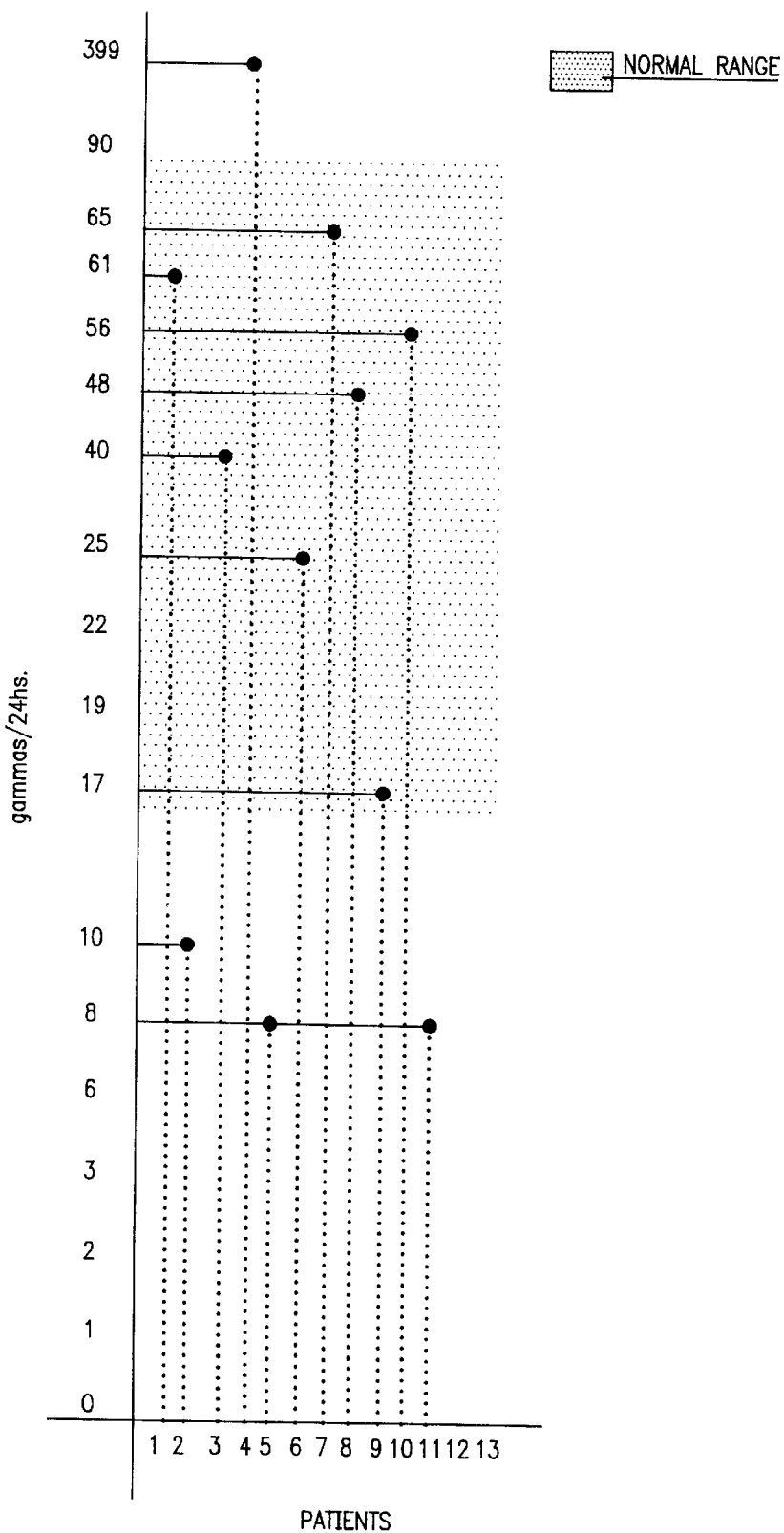
Figure 15:
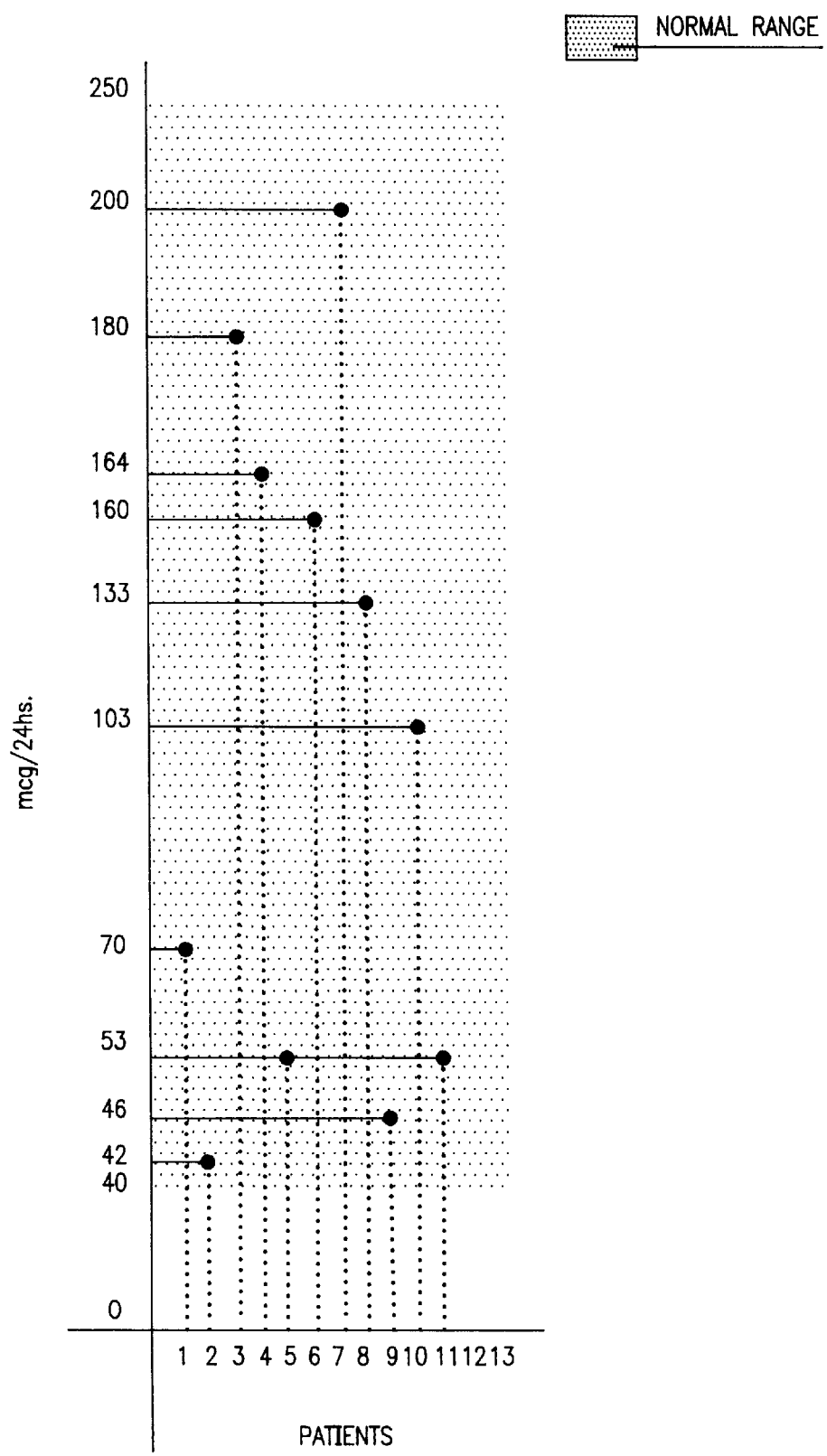
Figure 16:
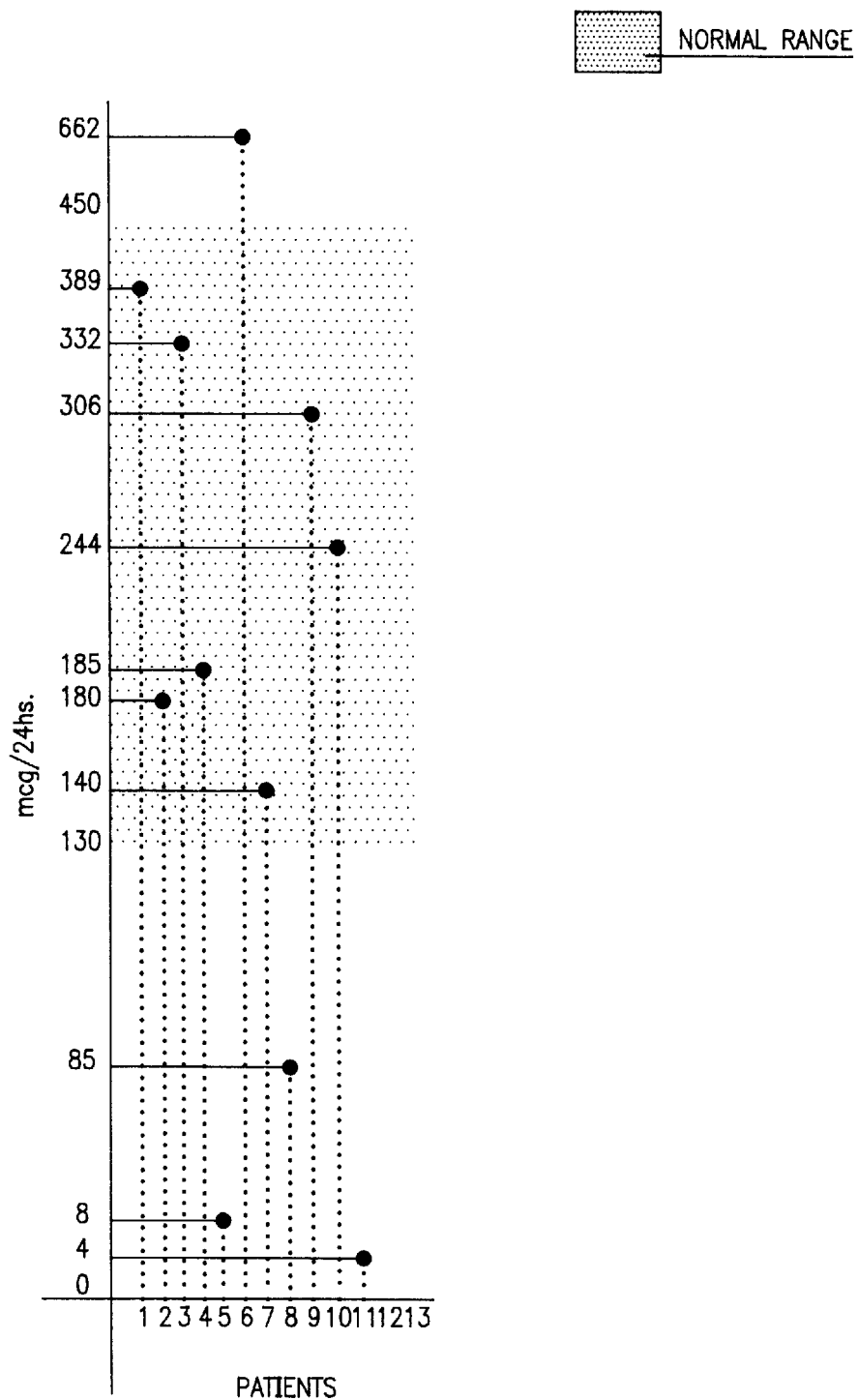
Figure 17:
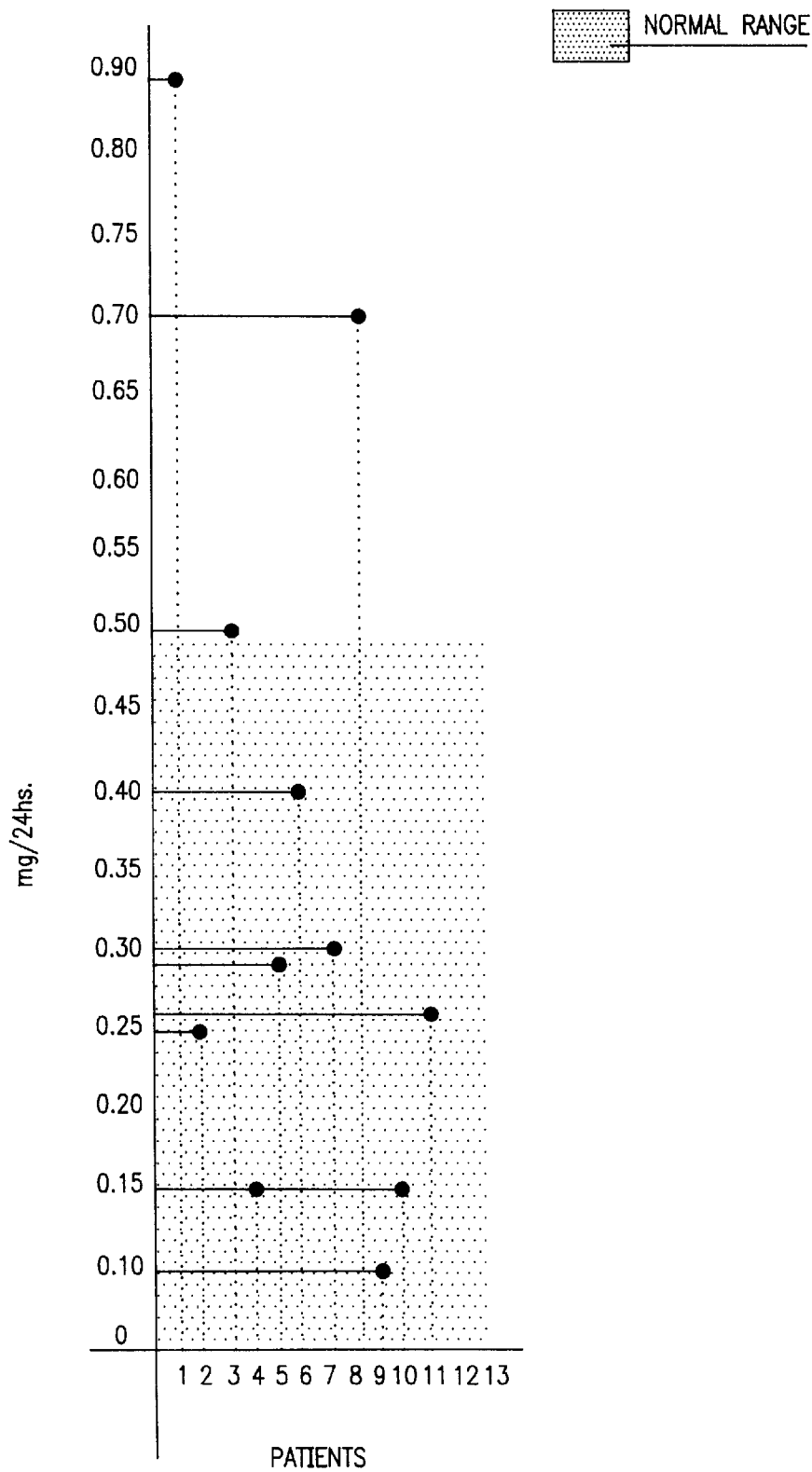
Figure 18:
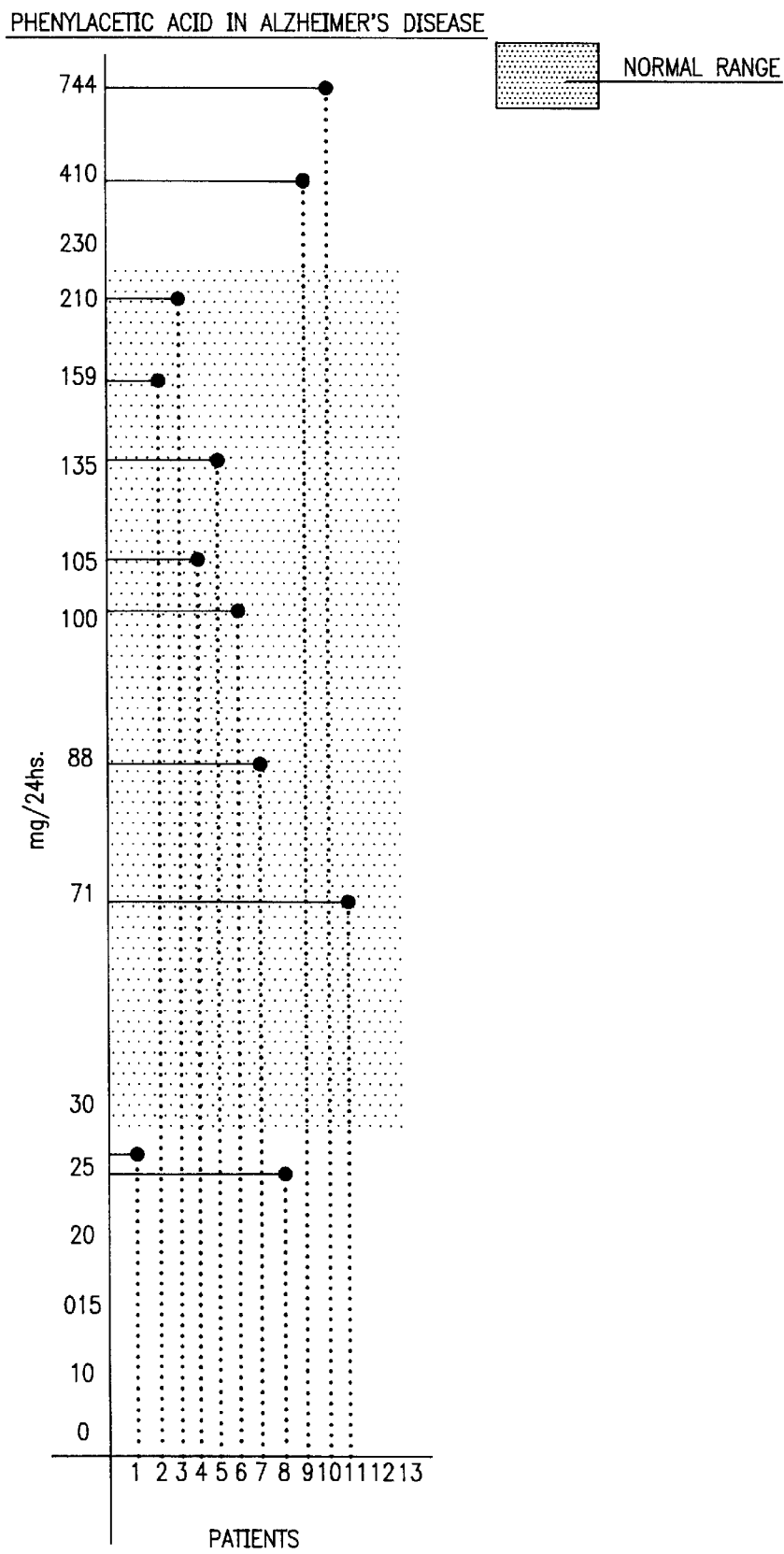

The observation, study and treatment of patients with pathological symptoms of diseases apparently so different from the point of view of the symptomatology of each one, as Alzheimer's Disease, Huntington's Chorea; observed chromosome anomalies such as deletion, fragility or other anomalies in the chromosomes and other pathologies which are mentioned further on, have allowed the applicant to establish that these diseases have a common denominator, consisting of a muscular hypotonia and lessened states of consciousness, at times progressive. They have also in common alterations in certain neurotransmitters.

These are pathological modifications, acquired or innate, variable in general according to age, sex, and the patient's state of health, with deviations in the degree and evolution of behavior according to each individual. The optional administration of benzodiazepines is according to the corresponding dosification in separate dosage.

Without treatment, this type of pathology evolves unfavorably, with a progressive deterioration of the cognitive capabilities and the capability of communication and social interchange.

In the course of the observation, study and comparison of the patients, including those who had been subjected, without success, to different conventional treatments, the applicant was able to observe perceptible improvements in patients treated in a contemporary manner with psycho pharmacological products: anti depressants, anti psychotics, neurotransmitters, and known neuroleptics. These improvements shown experimentally, have been interpreted as a synergistic manifestation of components administered simultaneously.

The experiences and treatments which were carried out have led to the formulation of a pharmaceutical composition which makes up one of the objectives of this invention and which includes the components a) to i), already mentioned, in an acceptable pharmaceutical vehicle.

Component a) is an anti psychotic formula(p.f.: 148–149), and its salts, especially Decanoate (commercially known as Neoperidol, KD-136 and Haldol Decanoate).

Component b) is Imipramine, an anti depressant whose formula: (p.f.: as chlorohydrate 174°–1750° C.), known commercially also as Tofranil-PM.

Component c) is Trifluoroperazine, another anti psychotic whose formula:

(p.f.:202°–210° C.) known commercially as Modaline, Triftazine.

These compounds, for the purposes of the current invention, can be used in the form of bases or acceptable pharmaceutical salts: inclusive in the form of N-oxide for Imipramine.

The isolated components are well known and in this respect not many explanations are needed. GABA (Gamma Amino Butyric Acid and its salts) is well known in the field of neurochemistry due to its antiarrhythmic effects.

The antioxidants mentioned when describing component f)—Ascorbic Acid (or ascorbates) and Vitamin E- are well known as inhibitors of the oxidizing effect of $O_2$ and especially of the free radicals formed in diverse biological processes, such as $O_2$, to which a preponderant role in the aging of the tissues is attributed Ascorbic Acid can also be utilized in the form of sodium ascorbate or also combined with nicotinamide (component 1) as ascorbic nicotinamide.

The isolated components, with the exception of Lithium, are vitamins or organic components. This is the case for Nicotinamide, a natural product in which Folic Acid, Nicotinamide, etc. coexist in variable proportions according to their origin.

This invention provides a method for treating symptoms of muscular hypotonia and diminished states of consciousness, and retarded maturity, in patients suffering from deletions, fragility or numeric chromosomic anomalies, cerebral or cerebellar atrophy, Huntington's Chorea or Alzheimer's Disease, and which entails administering effective non toxic doses, to patients, of the aforementioned components a) to i).

An effective quantity is for example a dose which is made up of:

0.01 to 3 mg of Haloperidol;
3 to 8 mg of Imipramine;
0.1 to 0.5 mg of Trifluoperazine;
0.05 to 200 mg of GABA;
Phenylalanine;
50 to 300 mg of anti oxidizing agents, such as Ascorbic Acid, Vitamin E or mixtures of the same;
100 to 300 mg of Folic Acid;
0.05 to 0.5 mg of Nicotinamide;
25 to 100 mg of Lithium Salts, such as Lithium Carbonate, Lithium Acetate, Bromide or Lithium Chloride.

More specifically, the method of this invention entails administering to patients suffering from symptoms of hypotonia, states of diminished consciousness and retarded maturity, effective non toxic doses which are made up of, at least, one of the following drugs:

a) 0.02 mg of Haloperidol;
b) 5 mg of Imipramine;
c) 0.2 mg of Trifluoroperazine; and also
d) 0.100 mg of Gamma Amino Butyric Acid;
e) 0.05 mg of Phenylalanine;
f) 200 mg of Folic Acid;
g) 0.100 mg of Nicotinamide;
h) 50 mg of Lithium Carbonate, in a pharmaceutically acceptable vehicle.

Obviously, the dosage is regulated according to the condition and state of the patient and the pathological symptoms shown.

This is a dosage of only one pill, if necessary divided and/or coated, in which the components are in a solid conventional medium as a vehicle. The different tablets encompass conventional solids, such as tablets, pills or coated pills.

Components a) to i) can be broken down into different units, which are administered simultaneously or at regular intervals. That is to say, that instead of administering one pill only which could be too large for one patient, the components can be distributed in two pills which can be administered at the same time or sequenced.

Another possible alternative is to administer components a) to i) in hard or soft gelatine capsules, in one only dose or in fragmented doses, such as has been indicated for tablets.

The pharmaceutical compositions of this invention are prepared by known methods using well known and easily acquired ingredients. For preparing the compounds of this invention, the components a) to i) are mixed with an excipient, diluted with an excipient or introduced in a carrier which can be in the form of a capsule or ampoule. The excipient can be of solid, semi solid or liquid material which acts as a vehicle for the active ingredient. In this way, the compounds can be found in the form of tablets, pills, powders, coated pills, water capsules, elixirs, suspensions, emulsions, solutions, including syrups.

Some examples of adequate excipients are Lactose, Dextrose, Saccharose, Sorbitol, Mannitol, starches, Gum Arabic, Calcium Phosphate, Algins, Tragacanth, gelatin, Calcium Silicate, micro crystalline cellulose, Polyvinylpyrrolidone, cellose, water, syrup, and Methyl cellulose. The formulations can also contain lubricating agents such as talcum powder, Magnesic Stearate and mineral oil, humectant agents, emulgents and suspending agents, preservatives such as Methyl and Propyl Hydroxybenzoate, sweeteners or flavouring agents. The compounds of this invention can be formulated for rapid, sustained or retarded release of the active ingredient after being administered to the patient, using well known procedures in this field.

EXAMPLES

After long and different tests were carried out on patients, these were divided into different groups:

1) Patients with an Alzheimer type of disease;
2) Patients with an unspecified retarded maturity;
3) Patients with Fragile X Syndrome;
4) Patients with Huntington's Chorea;
5) Patients with numeric anomalies in their chromosomes;
6) Patients with a deletion in some chromosome;
7) Patients with chromosomic fragility other than from the X chromosome;
8) Patients with atrophy in the brain or the cerebellum.

In each case the relatives of the patient were kept duly informed throughout the duration of the therapeutic tests.

Thus, in the case of an Alzheimer type of disease and in the cases of atrophy of the brain or the cerebellum, the test took 10 weeks with a control each 25 days. With the Fragile X syndrome and other chromosomic pathologies, the test was for 4 months with a monthly control, whilst with the unspecified retarded maturity and in Huntington's Chorea the test lasted 2 months with a monthly clinical control.

The studies which were carried out to make a diagnosis, varied according to the syndrome under study. Thus, all patients underwent a psychiatric interview and in the case of Alzheimer type diseases or others with atrophy in the central nervous system, a computed tomography of the brain, a cerebral mapping and urine levels of Adrenalin, Noradrenalin, Dopamine, Phenyl Acetic Acid, Dimethyltryptamine and Phenyl Ethylamine were requested.

In the case of retarded maturity, apart from the previous studies, a chromosomic and psychological study was made and the mental coefficient was established.

Once these studies were completed, the test treatment was started in accordance with the already established time schedules.

In this manner positive results were obtained:

Thus, in the Fragile X Syndrome, an improvement of 90% was obtained, whilst in the unspecified retarded maturity this percentage was reduced to 70%.

But apart from this it should be noted that in the Fragile X syndrome the improvement was much clearer and more significant in the cognitive area, as for example, patients began to speak, write and read, which they had been unable to do before. There are cases in the unspecified retarded maturity group who have improved almost as much as those patients with Fragile X, but these cases were fewer.

As for patients with Alzheimer's type diseases, they have been able to improve their speech, and recognize things and persons. Some of them were able to control their sphincters. In the case of women, they have been able to carry out household tasks.

The aforesaid can be illustrated in some examples. Beginning with patients suffering from Alzheimer type of diseases:

M.H., 63 years old, male

For five years he has been suffering depression, lack of memory and less vocabulary. He was a very lucid man, having been a Judge for many years. Computed tomography of the brain shows ventricular dilation. Cerebral mapping shows an alpha rhythm lateralized on the right. At the interview he was accompanied by his wife and doctor son. He previously received Imipramine and Lorazepam.

He improved his verbal expression, his vocabulary is much more ample and his recognition of members of his family has improved substantially. At 10 weeks his son noticed that he was more connected with his environment and with more capacity for reaction. At 13 weeks, his wife also found him more lucid and aware of his illness.

A year later, he continues to improve, becoming more lucid and able to handle money, something he had been unable to do.

He received: Haloperidol 0.02 mg; Imipramine 5 mg; Folic Acid 200 mg; Vit. E 150 mg; Phenylalanine 0.05 mg; Gaba 100 mg, one cap. twice a day.

V.A., 76 years old, female, is a painter

Approximately 2 years ago she began to notice a moderate loss of memory; nevertheless, she speaks well. Computed tomography of the brain shows ventricular dilation. She received Carbamazepine and Haloperidol.

She leads an active social life, even though she is unkempt in her personal appearance. The study of the neurotransmitters is within the normal limits. The cerebral mapping shows hyper volted waves; there is no focus nor paroxysm; there is a predomination of theta waves.

The study is abnormal as it shows disorganization of the cortical rhythms; hyper volted activity.

A month after beginning the treatment there were no changes and she had not gone back to painting; three months after beginning the treatment she began to paint again; she improved her humour and her memory; she watches T.V.; speaks more and at 20 months of treatment her diction is clear.

N.B., 78 years old, female

For two years she has been showing a clear alteration in her memory and on occasions not recognizing people. For the last 20 years she has been hyper tense and has a ventricular hypertrophy (with development of the aortic button).

Computed tomography of the brain shows diffuse encephalic cortical and central atrophy. She was treated with Cyanaricine and Imipramine between other.

The neuro metabolic study showed a somewhat low Dopamine, 160 mg (N 170–220) and a Phenylethylamine of 662 mg (N 130–450). Five weeks after stating treatment she began her household work spontaneously; at 2 months she began to cook and was in very good humour; at 3 months, having increased medication to 1 pill four times a day she improved far more and remembered recent happenings as also dates and days of the week; she is in very good humour.

After a year she is watching T.V. and is able to entertain herself; she has a good orientation.

In April 1993 she had a brief period of nocturnal enuresis.

August 1993 she had a pneumonopathy and a febrile convulsion.

In September 1993 she could not tolerate her lady companion; she had another febrile speak of 38° C. and a moderate hypertension of 170/90. She evolved well.

M.R., 47 years old, female

Is an atypical case; 10 years ago she started to feel insecure when walking, this became more accentuated five years ago. On the tomography a small osteoma was detected on the left posterior occipital.

Supercerebelosa cistern dilation. Magnetic nuclear resonance: a meningioma in the frontal prerolandic region and cerebellar atrophy were detected. At the time of the consultation she had severe difficulties in moving; she had to increase her base support a lot in order to walk which causes her to move insecurely and she speaks with a shaky voice.

Her mother died when she was 78 years old of Alzheimer's disease. The neurosurgeons follow her evolution and they have had a new magnetic resonance done to determine the evolution of the meningioma. The neurometabolic study is normal.

After a month and a half of treatment she speaks and walks better, something that is noticed by those close to her. In November 1993 the meningioma was operated on. She is well though a slight distress is noticed.

April 1994: there is a major atrophy of the cerebellum which confirms the one detected in 1992. This atrophy is bilateral with an increase in the pericentric cisterns.

November 1994: she continues well with her walking, speech and humour.

Patients with Fragile X Syndrome

S.B., 8 years old, male

Perinatal anoxia showed up; he had no convulsions; he was always very scatter brained and hyperactive; his mental coefficient was 60.

Electroencephalogram: showed diffuse bilateral disorganization of the cortical rhythms. His left hand has a simian line. He was treated with 15 mg of Folic Acid and 1 mg of Hydroxocobalamin.

Phenotype: long and prominent ears, the same as the frontal bone.

The karyotype shows 20% of Fragile X cells; 46 XY (20% fragility X, q27).

He was treated and his behaviour and scholastic achievements improved. He answers better and more rapidly, but he is somewhat irritable.

He received: Lithium carbonate 50 mg; Haloperidol 0.02 mg; Folic Acid 200 mg; Biotin 0.05 mg; Nicotinamide 0.100 mg; ATP 4 mg; Vit $B_1$ 3 mg; Vit $B_{12}$ 5 mcg, 1 cap. twice a day.

C.F., 7 years old, male

A patient who in kindergarten already showed learning and adaption difficulties. His behaviour was slightly hostile. He received Folic Acid 15 mg per day and GABA, 15 ml per day without any positive results.

Phenotype: long ears and moderate macro orquidism. The karyotype showed a chromosomic constitution 46,XY, (40% Fragile X cells).

His scholastic achievements changed substantially, though motor difficulties still are present.

G.G., 7 years old, male his parents noticed difficulties from kindergarten. He is hyperkinetic. He was treated with 10 mg of Folic Acid per day without any positive results.

Phenotype: long and prominent ears, slight macro orquidism.

Hyperkinetic, simian fold in the right hand; speaks with difficulty.

Karyotype: 46,XY (20% Fragile X cells).

After two months of treatment there was a notable improvement in school and he spoke better though his stuttering still persisted. The following year he continued improving at school and he passed his grade. Less hyperkinetic. After 4 years of treatment his evolution is excellent as far as learning and behaviour are concerned.

Patients with an unspecified retarded maturity

A.L., 6 years old, female

From the age of 4 her parents noticed that she did not learn. She is in first grade and cannot remember what she is being taught; she had no convulsions, neither she is aggressive. She received Carbamazepine 100 mg daily and Folic Acid 15 mg daily.

The karyotype was: 46,XX; X fragile negative.

In the metabolic study, made on the 22/10/91, a somewhat low Phenylalanine stands out, 123,9(N 130–450).

The 3 rd Nov. 1992 another similar study shows: Dopamine, 92(N 65–400); Phenylacetic Acid, 92 mg (N 100–200).

When medication was started she yawned with frequency. The medication was stopped for 72 hours. When the medication was started again she vomited; the medication was stopped again and later was resumed at half the dosage.

After 3 weeks her attention span improved; three months later she is more attentive at school and furthermore she plays and talks about her fantasies.

Two years later she continues doing well at school and her conduct has totally changed.

S.C., 6 years old, female

From the age of 3 her parents noticed difficulties, she did not speak. She had no convulsions, neither was she aggressive. She received Haloperidol 5 mg daily, Carbamazepine 50 mg daily and Folic Acid 20 mg daily.

Electroencephalogram normal.

Phenotype: only speaks a few words. Very hyperkinetic.

Karyotype: 46,XX; X Fragile negative.

Neurometabolic, outstanding is: Phenylacetic Acid, 8.3 mg (30–230); Phenylenylamine, 22.9 (N 130–450).

A month after starting treatment she began to quiet down and improve at school. In order to be able to vaccinate her against measles, medication was suspended for 5 days and in this lapse of time her behaviour became worse.

A year after treatment was started, her vocabulary, conduct and scholastic achievements changed substantially. In the three years that she has been undergoing treatment her achievements and improvements are very marked.

A Case Of A Patient With Chromosomopathy And Retarded Maturity

S.H., 15 years old, male

His parents are doctors, the studies which they brought showed a karyotype 47,XXY, but in a new karyotype which we carried out it showed that the chromosomic constitution was 48,XXYY. He was treated with Lorazepam 20 mg daily.

He was always under psychotherapy. His height is 191 cm and he weights 97 kg. From the age of two he has been physically aggressive. He completed primary school but dropped out in secondary.

He tells us that he has trouble understanding what he studies. Under medication he is under the impression of being somewhat sedated.

Two months after starting treatment his learning improved and he began computer lessons; he goes to dances which means he is more sociable.

Three months after treatment started a marked improvement is noted in his verbal expressions. He began working in a costume jewelry factory.

After three years of treatment he stopped coming and continued with social and work activity.

All these patients received a medication which was aimed at improving the symptoms which brought about the original consultation, and this has been successful in 90% of the patients with Fragile X syndrome; 72% in patients with unspecified retarded maturity, and 60% in patients with Alzheimer type diseases.

The medication was administered in doses of ½ a pill to 4 pills a day, made up from:

| Lithium Carbonate 50 | 50. mg. |
|---|---|
| Haloperidol | 0.02 mg. |
| Imipramine | 5. mg. |
| Folic Acid | 200. mg. |
| Vitamin E | 150. mg. |
| Ascorbic Acid | 0.5 g. |
| Phenylalanine | 0.05 mg. |
| Nicotinamide | 0.100 mg. |
| GABA | 100. mg. |

We claim:

1. A composition for treating a human subject having a disease associated with symptoms of unspecified retarded maturation which comprises
   a. in the amount indicated at least one member selected from the group consisting of 0.01 to 3 mg haloperidol, 3 to 8 mg imipramine and 0.1 to 0.5 mg trifluoperazine;
   b. 0.05 to 200 mg gamma amino butyric acid;
   c. 1 to 10 mg phenylalanine;
   d. 50 to 30 mg of an antioxidant selected from the group consisting of Vitamin E, ascorbic acid and mixtures thereof;
   e. 100 to 300 mg folic acid;
   f. 0.05 to 0.5 mg of a member selected from the group consisting of nicotinamide and its pharmaceutically acceptable salts; and
   g. 25 to 100 mg lithium salt; in a pharmaceutically acceptable carrier therefor.

2. A composition according to claim 1 comprising
   a. at least one member selected form the group consisting of 0.02 mg haloperidol, 5 mg imipramine and 0.2 mg trifluoperazine;
   b. 0.100 mg gamma amino butyric acid;
   c. 0.05 mg phenylalanine;
   d. 200 mg folic acid;
   e. 0.100 mg nicotinamide; and
   f. 50 mg lithium carbonate;
in a pharmaceutically acceptable carrier therefor.

3. A method of treating a human subject having a disease associated with symptoms of unspecified retarded maturation which comprises orally administering to such subject a therapeutic amount of the composition of claim 1.

4. A method of treating a human subject having a disease associated with symptoms of unspecified retarded maturation which comprises orally administering to such subject a therapeutic amount of the composition of claim 3.

5. A method of treating a human subject having a disease associated with symptoms of unspecified retarded maturation which comprises orally administering to the subject a therapeutic amount of the composition of claim 2 wherein said composition is administered in at least two divided doses.

6. A method according to claim 3 wherein said composition additionally includes a diazepine.

7. A method according to claim 3 wherein said composition is in tablet form and is administered to the subject in an amount of form ½ to 4 tablets per day.

* * * * *